United States Patent [19]

Hagiwara et al.

[11] Patent Number: 5,821,119
[45] Date of Patent: Oct. 13, 1998

[54] SHUTTLE VECTORS FOR ESCHERICHIA COLI AND CYANOBATERIA

[75] Inventors: Hideaki Hagiwara, Takarazuka; Yasunobu Takeshima, Kasai, both of Japan

[73] Assignee: Yoshihide Hagiwara, Takarazuka, Japan

[21] Appl. No.: 855,483

[22] Filed: May 13, 1997

Related U.S. Application Data

[63] Continuation-in-part of Ser. No. 329,144, Oct. 17, 1994, abandoned, which is a continuation of Ser. No. 946,415, Nov. 6, 1992, abandoned.

[30] Foreign Application Priority Data

Aug. 3, 1991 [JP] Japan ................................ 3-067774

[51] Int. Cl.$^6$ ........................... C12N 15/70; C12N 15/74; C12N 15/63
[52] U.S. Cl. .................... 435/320.1; 435/69.1; 435/172.3
[58] Field of Search ................................ 435/320.1, 69.1, 435/172.3, 252.3

[56] References Cited

PUBLICATIONS

Shinozaki et al. "Cloning and characterization of a plasmid DNA from Anacystis nidulans 6301", Gene 19:221–224, 1982.

Van der Plas et al. "Identification of replication and stability functions in the complete nucleotide sequence of plasmid pUH24 from the cyanobacterium Synechococcus sp. PCCC 7942", Molec. Microbiol. 6(5):653–664, 1992.

Gendel et al., J. Bacteriol. (1983), 156:148–154.

Williams, et al., Gene, (1983), 24:37–51.

Lightfoot, et al., J. Gen. Micobiol., (1988), 134:1509–1514.

Daniell, et al., Mol. Gen. Genet. (1986), 204:243:248.

Daniell, et al., Arch. Microbiol., (1989), 151:59–64.

Daniell et al. (1986) PNAS vol. 83: 2546–2550.

Sambrook et al. (1989) Molecular Cloning a lab manual Cold Spring Harbor Laboratory Press, NY.

*Primary Examiner*—Jasemine C. Chambers
*Assistant Examiner*—Scott D. Priebe
*Attorney, Agent, or Firm*—Sherman and Shalloway

[57] ABSTRACT

A vector plasmid containing
(a) the OriA region of plasmid pBA1 derived from Anacystis nidulans,
(b) the multicloning region and
(c) the region of colicin E1 plasmid, which contains the OriE region thereof and wherein the gene defined by the rop region thereof is removed.

This plasmid is replicable in the cells of both *Escherichia coli* and cyanobacteria and thus useful as a shuttle vector.

2 Claims, 4 Drawing Sheets

SHUTTLE VECTORS FOR ESCHERICHIA COLI AND CYANOBATERIA

This application is a continuation-in-part of application Ser. No. 08/329,144, filed Oct. 17, 1994, now abandoned which is continuation of Ser. No. 07/946,415, filed Nov. 6, 1992 which is based on International Application No. PCT/JP92/00267 filed on Mar. 6, 1992.

TECHNICAL FIELD

This invention relates to a novel plasmid, and relates in particular to a shuttle vector plasmid replicable in the cells of both *Escherichia coli* and cyanobacteria, which contains a DNA fragment containing the OriA region of plasmid pBA1 derived from *Anacystis nidulans*, a cyanobacterium.

BACKGROUND ART

A cyanobacterium *Anacystis nidulans* has a photosynthetic mechanism similar to those of higher plants, especially red algae, and can biosynthesize organic substances from water, carbon dioxide and slight inorganic salts and thus autotrophically proliferate. Further, *A. nidulans* is unicellular and makes colonies on an agar medium, and especially R2 strain tends to take DNAs into the cell and is thus possible to transform according to microbial and genetic methods.

Thus recently, many cloning vectors using endogenous plasmids in the *A. nidulans* R2 strain (for example, pUH24 and pUH25) have been developed [refer to C. A. M. J. J. von der Hondel et al. Proc. Natl. Acad. Sci. USA 77(3); 1570–1574 (1980); C. J. Kuhlemeier et al., Mol. Gen. Genet. 184:249–254 (1981); L. A. Sherman and P. van de Putte, J. Bacteriol. 150(1):410–413 (1982); S. Gendel et al., J. Bacteriol. 156(1):148–154 (1983); S. S. Golden and L. A. Sherman, J. Bacteriol. 155(3):966–972 (1983); C. J. Kuhlemeier et al., Plasmid 10:156–163 (1983); C. J. Kuhlemeier et al., Gene 31; 109–116 (1984); D. E. Laudenbach et al., Mol. Gen. Genet. 199:300–305 (1985); M. Y. Gruber et al., Curr. Microbiol. 15:265–268 (1987), etc.], and used for example for introduction of foreign genes and cloning of genes.

As examples of heterogenous proteins expressed using the strain R2 and known human carbonic anhydrase and the lac IQ repressor protein of *Escherichia coli* [G. D. Price and M. R. Badger, Plant Physiol. 91:505–513 (1989)], α-amylase of *Bacillus amyloliquefaciens* A50 [I. V. Elanskaya and I. B. Morzunoba, Mol. Genet. Microbiol. Virusol. 0(9):7-1 (1989) ], an insecticidal protein of *B. sphaericus* 1593M [N. Tandeau de Marsac et al., Mol. Gen. Genet. 209:396–398 (1987)], β-galactosidase of *Escherichia coli* [D. J. Scanlan et al., Gene. 90:43–49 (1990), M. R. Schaefer and S. S. Golden, J. Bacteriol. 171(7):3973–3981 (1989)], Mn-superoxide dismutase of *Escherichia coli* [M. Y. Gruber et al., Proc. Natl. Acad. Sci. USA 87:2608–2612 the (cI$^{ts}$ repressor protein of λ phage [D. Friedberg and J. Seiiffers, Mol. Gen. Genet. 203:505–510 (1986)], disaturase of a cyanobacterium Synechosystis PCC 6803 strain (des A) [H. Wada et al., Nature 347:200–203 (1990], etc.

On the other hand, *A. nidulans* 6301 has been developed using its endogenous plasmid (pBA1) vectors (shuttle vectors with *Escherichia coli*) such as pBAS 18 [12 kb, K. Shinozaki et al., Gene. 19:221–225 (1982)] and pBAS 5 [14 kb, Kazuo Shinozaki, "Shokubutsu Idenshi Sosa Gijutsu" (Plant Gene Manipulation Techniques), supervised by Hikoyuki Yamaguchi, pages 98 to 110, published by CMC]. *A. Nidulans* 6301 was deposited on Feb. 24, 1998, under deposit number FERM BP-6267, with the National Institute of Bioscience and Human-Technology (formerly the Fermentation Research Institute), Agency of Industrial Science and Technology. However, any of the vectors has difficult problems in gene manipulation, for example that the size of a gene capable of being inserted into any of the vectors is restricted because it has a length of 10 kb or more and each vector has only a small number of restriction endonuclease recognition sites usable for cloning. Further, the strain 6301 has a disadvantage that it does not easily take a gene DNA into its cell, compared with the strain R2, and as a result to transformation frequency is lower than that of the strain R2. As a method of enhancing the transformation frequency of the strain 6301, H. Daniell, et al. [Proc. Natl. Acad. Sci. USA 83:2546–2550 (1986)] propose that cells of the strain 6301 are treated with EDTA-lysozyme to convert them to permeaplasts, whereby they more easily take up DNAs. In fact, they succeeded in enhancing the transformation frequency of the strain 6301 using this method, but it has problems, for example, that the manipulation takes much time and is complicated and further the cells are easily damaged by the EDTA-lysozyme treatment.

Thus, for the purposes of enhancement of the transformation frequency of *A. nidulans* 6301, construction of a plasmid easy to handle on gene manipulation, etc., the present inventors, first, intensely studied for miniaturization of a plasmid, succeeded in creating a plasmid capable of remarkably enhancing the transformation frequency of the strain 6301 by making as small as possible the parts other than the replication initiation region of an endogenous plasmid (pBA1) of the strain 6301 as a base and at the same time by combining the resulting plasmid with a DNA fragment which contains the replication initiation region of the Col. E1 plasmid of *Escherichia coli* (OriE. region) and wherein a gene defined by the rop region (this region is also called rom region but referred to as rop region in the present specification) is removed, and further the multicloning region being used in pUC 18, and completed this invention.

DISCLOSURE OF THE INVENTION

Thus according to this invention is provided a shuttle vector plasmid replicable in *Escherichia coli* and cyanobacteria, which contains (a) the OriA region of plasmid pBA1 derived from *Anacystis nidulans*, (b) the multicloning region and (c) the region of colicin E1 plasmid, which contains the OriE region thereof and wherein the gene defined by the rop region thereof is removed. The shuttle vector plasmids of this invention, when used to transform *A. Nidulans*, as described below, are incorporated in large copy number and remain stable, but without being integrated into the genome of the host cell.

The plasmid of this invention is further detailedly described below.

"The OriA region of plasmid pBA1 derived from *Anacystis nidulans*" (hereinafter sometimes abbreviated as "OriA") constituting the plasmid of the invention is a gene fragment containing the replication initiation region derived from plasmid pBA1 which is the plasmid having a molecular weight of $(5.04\pm0.26)\times10^6$ (by electron microscope analysis) or $5.2\times10^6$ (by agarose gel electrophoresis analysis) [K. Shinozaki et al., Gene., 19:221–224 (1982)] between the two endogenous plasmids of *Anacystic nidulans* 6301 (Synechococcus PCC 6301, ATCC 27144, UTEX 625 strain) belonging to the genus cloococcus, blue-green algae, and its size can generally be in the range of 2.8 to 8.0 kb., preferably 2.8 to 4.4 kb. Specific examples thereof are an OriA region-containing DNA fragment having a size of about 4.4 kb obtained by cutting pBA1 with restriction endonucleases XhoI and BamHI, an OriA region-containing DNA fragment having a size of about 3.3 kb obtained by cutting pBA1 with PvuII and BamHI, etc.

The "multicloning region" (hereinafter sometimes abbreviated as "MC region") is a sequence (which is also called a polylinker) having various restriction endonuclease recognition sites. An example thereof is Col E1 plasmid pUS used as an *Escherichia coli* cloning vector, e.g., a DNA fragment of 55 bp having restriction endonuclease recognition sites of EcoRI, SacI, KpnI, SmaI, XmaI, BamHI, XbaI, SalI, AccI, HincII, PstI, SphI and Hind III. Further, MC regions derived from pUS 12, pUC 13, pUC 19, etc., and a MC region derived from a phage vector M 13 of *Escherichia coli* are also available. Still further, chemically synthesized MC regions are also available.

Further, "a region derived from Col E1 plasmid which contains the OriE region and wherein the gene defined by the rop region is removed" (hereinafter sometimes abbreviated as "OriE") used in combination with the OriA and MC regions in the invention means the replication initiation region of a Col E1 plasmid which is used in *Escherichia coli* and whose copy number is 20 to 30 per cell body. A representative example of such OriE is an OriE-containing DNA fragment which can be cut out from plasmid pBR 322 with restriction endonuclease PvuII, AvaI, BamHI, Eco 47III, EcoRV, PstI, etc., and whose size is 1.5 to 4.1 kb, preferably 1.5 to 2.5 kb, and there can further be used OriE-containing DNA fragments derived from plasmids pUC 18, etc.

Further, these OriE-containing DNA fragments can contain drug resistance genes such as an ampicillin resistance gene (Amp$^r$) which can be a marker in cloning.

So long as a plasmid provided by this invention has DNA fragments containing respectively the afore-mentioned three essential gene regions, i.e., OriA, MC region and OriE, it can further contain DNA fragments carrying other genetic information, for example a DNA fragment containing an ampicillin resistance gene, an antibiotic resistance marker and/or a DNA fragment containing a chloramphenicol resistance gene, or an antibiotic resistance marker. Typical examples of such plasmids are two plasmids named "plasmid pBAX 18" and "plasmid pBAX 20" respectively by the present inventors which substantially comprise DNA fragments containing three gene regions of OriA, MC region and OriE respectively and whose molecular weights are about 4.48 MDa (about 6.9 kb) and about 3.76 megadaltons (about 5.8 kb) respectively.

In the present specification, the molecular weight of plasmids is a value measured by the agarose gel electropheresis method.

These plasmids pBAX 18 and pBAX 20 are more detailedly described below.

Figure 1:
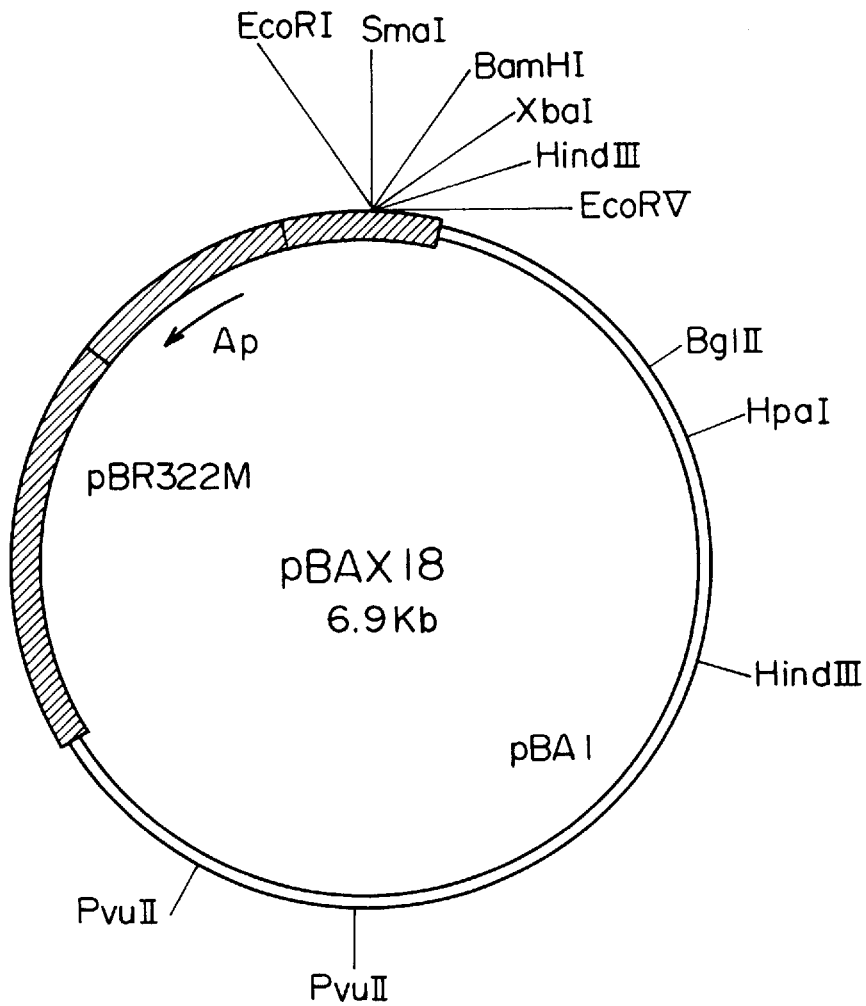
FIG. 1 is a restriction endonuclease map of plasmid pBAX 18.
Figure 2:
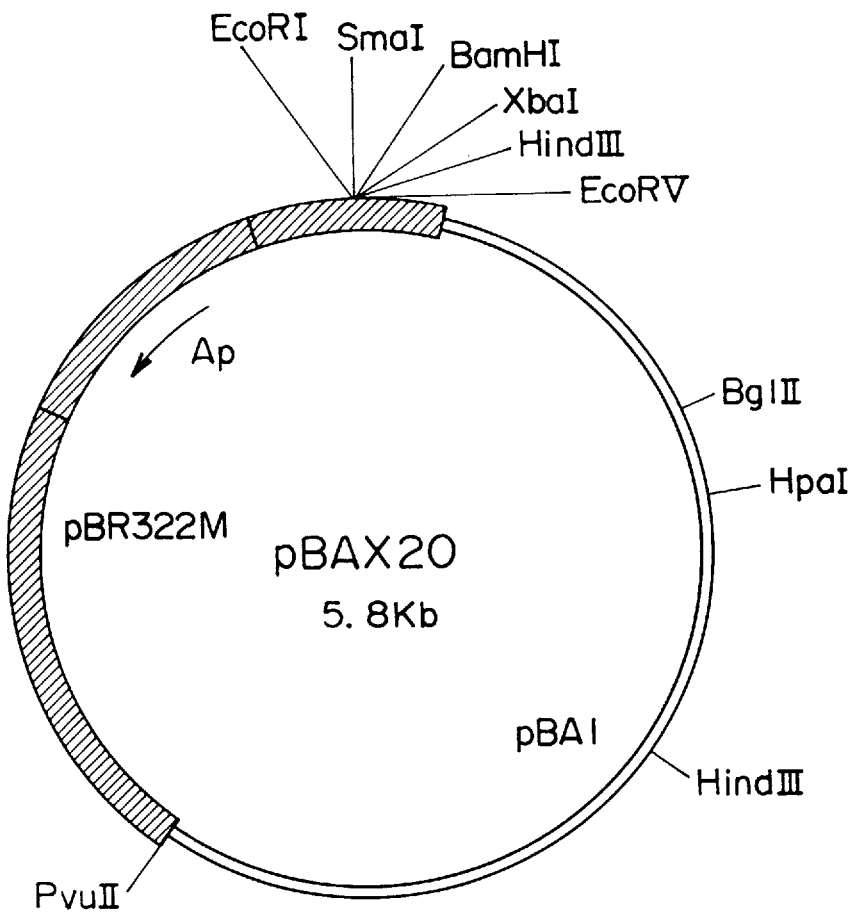
FIG. 2 is a restriction endonuclease map of plasmid pBAX 20.

The numbers of recognition sites of plasmids pBAX 18 and pBAX 20 with various restriction endonucleases and the lengths (kb) of digested fragments thereof with the restriction endonucleases are as shown in the following Table 1. Further, the restriction endonuclease maps of plasmids pBAX 18 and pBAX 20 are shown in FIGS. 1 to 2.

TABLE 1

| Restriction endonuclease | Plasmid pBAX 18 | | Plasmid pBAX 20 | |
| --- | --- | --- | --- | --- |
| | Number of Recognition Sites | Length of digested fragments (kb) | Number of Recognition Sites | Length of digested fragments (kb) |
| EcoRI | | 6.9 | 1 | 5.8 |
| BamHI | 1 | 6.9 | 1 | 5.8 |
| XbaI | 1 | 6.9 | 1 | 5.8 |
| SmaI | 1 | 6.9 | 1 | 5.8 |
| BglII | 1 | 6.9 | 1 | 5.8 |
| HpaI | 1 | 6.9 | 1 | 5.8 |
| EcoRV | 1 | 6.9 | 1 | 5.8 |
| ScaI | 1 | 6.9 | 1 | 5.8 |
| PvuII | 2 | 6.4, 0.45 | 1 | 5.8 |
| HindIII | 3 | 5.1, 1.5, 0.3 | 3 | 4.0, 1.5, 0.3 |
| KpnI | 4 | 2.8, 1.7 1.5, 0.84 | 3 | 3.3, 1.7 0.84 |
| PstI | 5 | 3.8, 1.45 0.85, 0.55 0.25 | 5 | 2.7, 1.45 0.88, 0.55 0.25 |

The plasmids pBAX 18 and pBAX 20 of this invention having the above-mentioned characteristics can, for example, be prepared as follows.

First, the OriA-containing DNA fragment of plasmid pBA 1 derived from *Anacystic nidulans* can be prepared, for example, by cloning a shuttle vector pBAS 18 in *Anacystic nidulans* and *Escherichia coli* [refer to K. Shinozaki et al., Gene 19:221–224 (1982)] in *Escherichia coli* according to a conventional method (T. Maniatis et al., Molecular Cloning-a Laboratory Manual-, published by Cold Spring Hobor Laboratory), and then cutting DNA fragments out from the cloned plasmid pBAS 18 according to a Conventinal method (T. Maniatis et al., Molecular Cloning) and using the combination of restriction endonuclease BamHI and XhoI or the combination of restriction endonucleases BamHI and PvuII. Thereby, OriA-containing DNA fragments are obtained having sizes of about 4.1 kb and about 3.3 kb respectively. The 5' projecting end of these DNA fragments can be blunted by $T_4$ DNA polymerase, if necessary.

On the other hand, the MC region of plasmid pUC can, for example, be prepared by cutting it out from plasmid pUC 18 with restriction endonucleases EcoRI and Hind III.

Further, it is convenient to use plasmid pBR 322, a typical Col E1 plasmid as a source of the DNA fragment which contains the OriE region of Col E1 plasmid and wherein the gene defined by the rop region is removed.

The thus prepared MC region is combined with the restriction endonucleases EcoRI and Hind III-treated plasmid pBR 322, and $T_4$ DNA ligase is made to act thereon to prepare plasmid pBR 322M wherein the above MC region is integrated into plasmid pBR 322. Then, a DNA fragment of about 2.5 kb which is obtained by treating this plasmid pBR 322 M with restriction endonuclease Eco 47III and PvuII and contains both OriE and MC region is combined with the OriA-containing DNA fragment prepared as above, and T4 DNA ligase is made to act thereon to obtain the desired plasmids pBAX 18 and pBAX 20.

Figure 3:
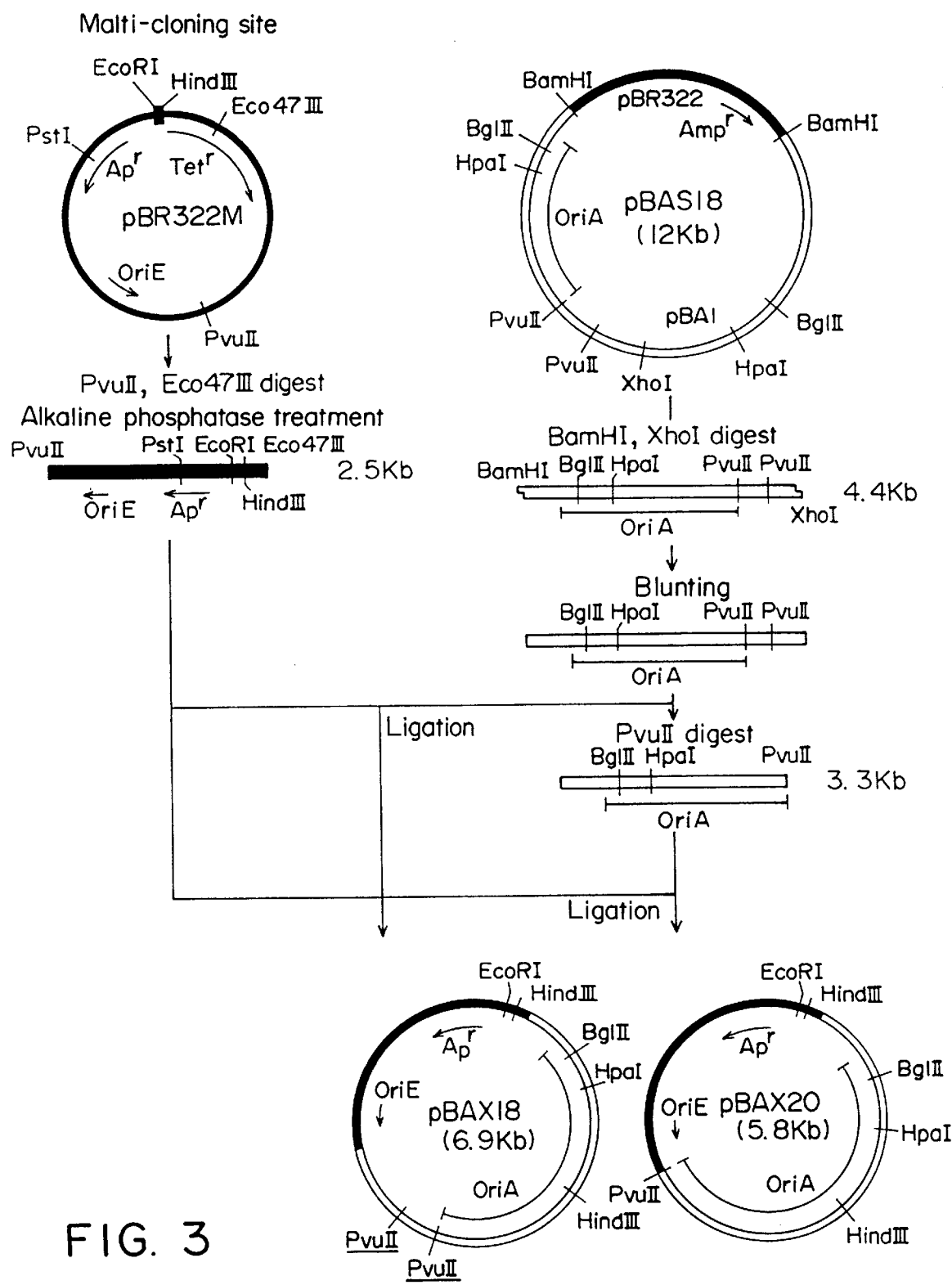
FIG. 3 is a construction drawing of plasmids pBAX 18 and pBAX 20.

The construction drawing of plasmids pBAX 18 and pBAX 20 are shown in FIG. 3 and more specific preparation methods thereon are in more detail described later in examples.

Thus prepared plasmids of this invention are shuttle vectors having the OriE region making its autonomous replication in the cells of Escherichia coli possible and the OriA region making its autonomous replication in the cells of Anacystis nidulans possible. Therefore, the plasmids of the invention can be prepared in a large amount using Escherichia coli proliferating in a high speed, and by using the plasmid DNA thus prepared in a large amount it is possible to efficiently and stably and in large copy number transform cells of cyanobacteria such as Anacystis nidulans.

Further, since the multicloning region is introduced in the plasmid of the invention, as recognition sites for inserting (foreign) genes recognition sites such as SmaI, BamHI, XbaI, ScaI and EcoRV are utilizable in addition to the EcoRI recognition site solely used in plasmid pBAS 18.

Further, the plasmid of the invention can be miniaturized up to about a half in size (6.9 kb to 5.8 kb) of plasmid pBAS 18 (12 kb) because the DNA parts other than the OriA region of plasmid pBA1 is removed in the present plasmid. Consequently, it is possible to introduce into the plasmid of the invention a (foreign) gene larger than a (foreign) gene which can be introduced into plasmid pBAS 18.

Introduction of the plasmid of this invention having the above characteristics on gene manipulation into a host cell can be carried out by a method known per se, for example by a method disclosed in literatures such as D. A. Lightfoot et al., J. General Microbial 134: 1509–1514 (1988).

The transformation frequency of the thus transformed Anacystis nidulans 6301 can be about 1,000-fold, compared with the value when the strain was transformed with plasmid pBAS 18. Therefore, by using the plasmid of the invention it is possible, even when a (foreign gene) is inserted, to easily select cells having the plasmid wherein the desired gene is inserted.

Mentioned as structural genes capable of being integrated into the plasmid of the invention are structural genes derived from Anacystis nidulans, structural genes derived from other cyanobacteria cells, structural genes derived from other bacteria, structural genes derived from higher animals and plants, etc., and thus therein origins are not limited at all. Further, chemically synthesized structural genes may also be utilized as structural genes capable of being integrated into the plasmid of the invention. Examples of such genes are chemically synthesized human superoxide dismutases [h-SOD, h-SOD-Ala[6] (refer to Japanese Laid-Open Patent Publication No. 156884/1990, etc.].

The plasmid of this invention is more specifically described below according to examples.

EXAMPLE 1

(1) Introduction of a multicloning site (derived from pUC 18) into pBR 322

A) EcoRI-Hind III digestion and alkaline phosphatase treatment of pBR 322

To 20 μl (10 μg) of a pBR 322 DNA solution were added 40 μl of a 5×Hind III buffer (50 mM Tris-HCl (pH 7.5), 35 mM MgCl$_2$, 300 mM NaCl), 80 units (10 μl) of Hind III (produced by Takara Shuzo Co., Ltd.) and 130 μl of sterilized water, and the mixture was subjected to incubation at 37° C. for 2 hours. After the reaction, to the resulting solution were added to 40 μl of a 5×EcoRI buffer (500 mM Tris-HCl (pH 7.5), 35 mM MgCl$_2$, 250 mM NaCl, 35 mM 2-mercaptoethanol, 0.05% bovine serum albumin), 120 units (10 μl) of EcoRI (produced by Takara Shuzo Co., Ltd.) and 50 μl of sterilized water, and the mixture was subjected to reaction at 37° C. for 2 hours. After the reaction, the mixture was subjected to phenolchloroform treatment and ethanol precipitation, and the resulting DNA was collected and dissolved in 100 μl of 0.1M Tris-HCl (pH 8.0). To this solution was added 10 μl of an alkaline phosphatase (produced by Takara Shuzo Co., Ltd.) solution (1 unit/10 μ2l alkaline phosphatase, 10 mM Tris-HCl (pH 7.5), 50 mM NaCl, 1 mM ZnSO$_4$), and the mixture was subjected to incubation at 37° C. for 1 hour. After the reaction, 10 μl of the alkaline phosphatase solution was further added and the mixture was further subjected to incubation at 65° C. for 30 minutes. The resulting solution was treated with phenol-chloroform and then subjected to ethanol precipitation, and the resulting DNA was recovered.

B) Isolation of a multicloning site (EcoRI-Hind III) from pUC 18

Two Eppendorf tubes were prepared each of which contained 30 μl (20 μg) of a pUC 18 DNA solution to which had been added 20 μl of a 10×K buffer (200 mM Tris-HCl (pH 8.5), 100 mM MgCl$_2$, 10 mM DTT, 100 mM KCl), 80 units (10 μl) of Hind III and 140 μl of sterilized water and which contained the mixture, and each mixture therein was subjected to incubation at 37° C. for 3 hours. After the reaction, the mixture was treated to phenol-chloroform and subjected to ethanol precipitation, and the resulting DNA was collected and dissolved in 112.5 μl of sterilized water. To each of the resulting solutions were added 30 μl of a 5×EcoRI buffer and 190 units (7.5 μl) of EcoRI, and the mixture was subjected to incubation at 37° C. for 3 hours. DNAs were precipitated with ethanol and recovered and subjected to 1.5% agarose gel electrophoresis to separate the desired DNA fragment (about 50 bp). This DNA was electrically eluted from the gel, treated with phenol-chloroform and purified by ethanol precipitation.

C) Ligation of pBR 322 (digested with EcoRI-Hind III) to the multicloning region To 0.2 μg (1 μl) of pBR 322 (EcoRI-Hind III, AP treatment) DNA and 0.2 μg (1 μl) of the multicloning site DNA were added 1 μl of TE (10 mM Tris-HCl (pH 8.0), 1 mM EDTA) and 24 μl of the Takara ligation kit A solution, and the mixture was sufficiently stirred. To this solution was added 3 μl of the Takara ligation kit B solution and the mixture was subjected to incubation at 16° C. for 4 hours.

D) Cloning of plasmid pBR 322M

To 3 μl of (40 ng) of the resulting ligation solution above was added 200 μl of a cell suspension of E. coli HB 101 treated with 50 mM CaCl and the mixture was gently mixed. This mixture was subjected to incubation in ice water for 30 minutes and then to incubation at 42° C. for 2 minutes to make the cells take DNAs therein. To this suspension was added 1.8 ml of a 2YT (16 g/l tryptone, 10 g/l yeast extract, 5 g/l NaCl) liquid medium, and the mixture was subjected to shaking culture at 37° C. for 1 hour and then plated on a LB (10 g/l trypton, 8 g/l NaCl, 5 g/l yeast extract) agar medium (containing 50 μg/ml ampicillin). Plasmids were prepared from the resulting colonies and their restriction endonuclease maps were analyzed to screen colonies having the desired plasmid (pBR 322M). The screened colonies were cultured in 200 ml of a 2YT liquid medium (containing 100 μg/ml ampicillin) and the plasmid DNA was prepared in a large amount according to the SDS-alkali method.

(2) Isolation of PvuII-Eco 47III fragment (2550 bp)

Three Eppendorf tubes were prepared containing 10 μg (10 μl) of pBR 322M plasmid DNA prepared in the above (1) and to which were added 20 μl of a 10×M buffer (100 mM Tris-HCl (pH 7.5), 100 mM MgCl$_2$, 10 mM DTT, 500 mM NaCl), 120 units (10 μl) of PvuII (produced by Takara Shuzo Co., Ltd.) and sterilized water to make the total volume of 200 μl. These tubes were subjected to incubation at 37° C. for 3 hours. After the reaction, the mixtures were treated with phenol-chloroform, and DNAs were collected by ethanol precipitation and dissolved in 174 μl portions of sterilized water, respectively. To these solutions were added 20 μl portions of a 10×H buffer and 24 units portions of Eco47 III (produced by Takara Shuzo Co., Ltd.), and the mixtures were incubated at 37° C. for 3 hours, respectively. DNAs were recovered by ethanol precipation and the desired DNA fragment (2550 bp) was separated by 1.5 % agarose gel electroporesis. The separated DNA fragment was purified using Geneclean and formed into 50 μl of a 0.1M Tris-HCl (pH 8.0) solution. To this solution was added 5 μl of an alkaline phosphate solution and the mixture was subjected to incubation at 37° C. for 1 hour. After the reaction, 5 μl of the alkaline phosphate solution and the mixture was further subjected to incubation at 65° C. for 30 minutes. After the reaction, the mixture was subjected to phenolchloroform treatment and subsequent ethanol precipitation, and the resulting DNAs were collected and dissolved in 20 μl of TE.

(3) Separation of the replication initiation point in *A. nidulans* of pBAS 18

Into *E. coli* HB 101 was introduced the shuttle vector pBAS 18 (K. Shinozaki et al., Gene 19:221–224 (1982)) a recombinant plasmid containing *Escherichia coli* and *A. nidulans* DNA, wherein an endogenous plasmid (pBA 1, digested with BamHI) of *A. nidulans* 6301 strain had been inserted into the BamHI site of pBR322. The resulting strain was cultured in an LB liquid medium (containing 50 μg/ml ampicillin) and the vector plasmid was prepared in a large amount using the SDS-alkali method. To 14 μg (20 μl) of the prepared pBAS 18 DNA were added 20 μl of a 10×K buffer, 100 units (10 μl) of BamHI (produced by Takara Shuzo Co., Ltd.) and sterilized water to make the total volume of 200 μl in an Eppendorf tube. Three Eppendorf tubes were prepared containing the same contents as above, and the contents were subjected to incubation at 30° C. for 3 hours. After the reaction, DNAs were recovered by ethanol precipitation, and the desired DNA fragment (pBA 1, about 8.0 kbp) was separated by 1% agarose gel electrophoresis and purified by Geneclean. To 2 μg (5 μl) of the separated and purified pBA 1 (digested with BamHI) DNA were added 5 μl of a 10×K buffer, 24 units (2 μl) of XhoI (produced by Takara Shuzo Co., Ltd.) and 38 μl of sterilized water, and the mixture was subjected to incubation at 37° C. for 3 hours. After the reaction, the mixture was treated with phenol-chloroform and the DNA was collected by ethanol precipitation. Both ends of the obtained DNA which is a digest of pBA1 with BamHI-XhoI were blunted using the Takara Blunting kit.

(4) Construction of a miniaturized *E. coli*—*A. nidulans* shuttle vector pBAX 18 (6.9 kbp)

To 40 ng (2 μl) of the blunted DNA and 200 ng (4 μl) of the PuvII-Eco47III fragment DNA was added 48 μl of the Takara ligation kit A solution, followed by sufficient stirring. 6 μl of the B solution was added and incubation was carried out at 16° C. for 4 hours. The *E. coli* HB 101 strain was transformed using this solution and then plated on an LB agar medium (containing 50 μg/ml ampicillin and 1.5% agar) to obtain colonies. Plasmids were prepared from the obtained colonies and analyzed for restriction endonuclease mapping to screen colonies carrying the desired plasmid pBAX 18. The screened colonies were cultured in 45 ml portions of a 2YT liquid medium (containing 100 μg/ml ampicillin) and the plasmid DNA was prepared by the SDS-alkali method.

(5) Preparation of pBAX 20 (about 5.8 kb)

To 1 μg (4 μl) of BamHI-XhoI (blunted) DNA fragment prepared in (3) were added 2 μl of a 10×M buffer, 1 μl (12 units) of PvuII and 13 μl of sterilized water, and incubation was carried out at 37° C. for 3 hours. To 2 μl (100 ng) of this reaction solution were added 100 ng (2 μl) of the PvuII-Eco 47 DNA fragment prepared in (2) and 16 μl of Takara ligation Kit A solution, and after sufficient stirring the B solution was added and then incubation was carried out at 16° C. for 2 hours. After the reaction, *E. coli* HB 101 strain was transformed using this solution and plated on an LB agar medium (containing 50 μg/ml ampicillin and 1.5% agar) to obtain colonies. Colonies carrying the desired plasmid (pBAX 20) were screened from the obtained colonies and cultured in 200 ml of a 2YT liquid medium (containing 100 μg/ml ampicillin) and the plasmid DNA was prepared by the SDS-alkali method.

EXAMPLE 2

Transformation of *A. nidulans* 6301

Cells cultured in 100 ml of a BG-11 liquid medium for 1 to 5 days were collected by centrifugation at 8,000 rpm for 5 minutes and suspended in 10 ml of a fresh liquid medium at a concentration of $10^8$ to $10^9$ cells/ml). One ml portions of this cell suspension were poured into polyethylene tubes (Falcon 2059), and the plasmid DNAs prepared in Example 1 were added in the respective tubes in a concentration of 1 μg (pBAS 18 is 10 μg). These tubes were covered with aluminum foils respectively, culture was carried out at 30° C. overnight, the aluminum foils were removed, and culture was further continued at 30° C. under irradiation with light (1,000–2,000 luxes). These cell suspensions were diluted 5-fold (those to which pBAS 18 had been added were not diluted) and plated in 100 to 500 μl proportions thereof on a BG-11 agar medium (containing 1 μg/ml ampicillin and 1 mM sodium thiosulfate and 1.5% agar). These plates were cultured under irradiation with light (2,000–3,000 luxes) for 4 to 10 days.

The transformation frequency of the thus obtained colonies were $10^{-3}$ to $10^{-4}$ cells/μg plasmid DNA in case where the plasmids of the invention were used, and thus about 1,000-fold frequencies were obtained, compared to the case ($10^{-7}$ cells/μg plasmid DNA) where plasmid pBAS 18 was used. In the transformed *A. nidulans* using the plasmids of this invention the plasmids remain stable and are present in large copy number.

EXAMPLE 3

Isolation of pBA1 plasmid from *A. Nidulans* 6301 strain:

*A. Nidulans* 6301 strain cultured in 300 ml of BG-11 medium was collected by centrifugation at 10,000 rpm for eight minutes, and suspended in 30 ml of SET solution (50 mM Tris-HCl, 50 mM EDTA, 20% sucrose, pH 7.6). 60 mg of lysozyme was added to the resulting suspension and, then, incubation was conducted at 37° C. for two hours. Next, proteinase K was added to make its concentration become 100 μg/ml. Thereafter, the suspension was incubated for another 16 hours. A lytic mixture (1% SDS, 0.2N NaOH) was added to this reaction liquid. After completion of bacteriolysis, the intended endogenous plasmid DNA was extracted and formed by means of a normal SDS-alkali method. The intended plasmid pBA1 was isolated from the obtained plasmid DNA by electrophoresis with use of 0.8% agarose gel. After the electrophoresis was finished, the DNA bands which seemed to be pBA1 were cut out from the gel stained with ethidium bromide on a trans-illuminator, and the intended plasmid DNA was eluted from the gel and purified by use of GENECLEAN™.

EXAMPLE 4

(1) Preparation of pBAS10 and pBAS10R (about 10.1 kb):

Both ends of 2 μg of the pBA1 (digested with BamH1) DNA prepared in Example 1(3) were blunted using a Takara Blunting Kit. 48 μl of Takara Ligation Kit A solution was added to 40 ng (2 μl) of this blunted DNA and 200 μg (4 μl) of the PvuII-Eco 47III fragment DNA of the pBR 322 prepared in Example 1(2). After sufficient stirring, 6 μl of the B Solution of the Takara Ligation Kit was added. The resulting mixture was incubated at 16° C. for four hours. E. Coli HB 101 strain was transformed using this solution and plated on an LB agar medium (containing 50 μg/ml ampicillin and 1.5% agar) to obtain colonies. Plasmids were prepared from the obtained colonies. The colonies carrying the intended plasmids pBAS10 and pBAS10R (pBAS10 and pBAS10R differ from each other in the direction in which pBA1 fragment is inserted) were screened by analyzing the restriction map. The screened colonies were each cultured in 45 ml of a 2YT liquid medium (containing 100 μg/ml of ampicillin), and the plasmid DNA was prepared by the SDS-alkali method.

(2) Preparation of pBAX10 and pBAX10R (about 8.8 kb)

Both ends of BamHI-digested DNA of pBR322 prepared in Example 1(3) were blunted using the Takara Blunting Kit. 48 μl of Takara Ligation Kit A solution was added to 200 μg (4 μl) of this blunted DNA and 40 ng (2 μl) of the blunted and BamHI-XhoI-digested DNA of the pBA1 prepared in Example 1(3). After sufficient stirring, 6 μl of the B Solution of the Takara Ligation Kit was added. The resulting mixture was incubated at 16° C. for four hours. E. Coli HB 101 strain was transformed using this solution and plated on an LB agar medium (containing 50 μg/ml ampicillin and 1.5% agar) to obtain colonies. Plasmids were prepared from the obtained colonies. The colonies carrying the intended plasmids pBAX10 and pBAX10R (pBAX10 and pBAX10R differ from each other in the direction in which BamHI-XhoI fragment is inserted) were screened by analyzing the restriction map. The screened colonies were each cultured in 45 ml of a 2YT liquid medium (containing 100 μg/ml of ampicillin), and the plasmid DNA was prepared by the SDS-alkali method.

(3) Preparation of PBAX18R (about 6.9 kb):

48 μl of Takara Ligation Kit A solution was added to 40 ng (2 μl) of the blunted BamHI-XhoI fragment DNA prepared in Example 1(4) and 200 μg (4 μl) of PvuII-Eco47III fragment DNA prepared in Example 1(2). After sufficient stirring, 6 μl of the B Solution of the Takara Ligation Kit was added. The resulting mixture was incubated at 16° C. for four hours. E. Coli HB 101 strain was transformed using this solution and plated on an LB agar medium (containing 50 μg/ml ampicillin and 1.5% agar) to obtain colonies. Plasmid DNAs were prepared from the obtained colonies. The colonies carrying the intended plasmid pBAX18R were screened by analyzing the restriction map. The screened colonies were each cultured in 45 ml of a 2YT liquid medium (containing 100 μg/ml of ampicillin), and the plasmid DNA was prepared by the SDS-alkali method.

(4) Transformation of Anacystis nidulans R2 strain:

The cells cultured to the logarithmic growth phase in 100 ml of a BG-11 medium were collected by centrifugation at 8,000 rpm for 5 minutes and suspended in a fresh liquid medium to $2\times10^8$ cells/ml (O.D.$_{730}$=0.5). This cell suspension was poured into polypropylene tubes (Falcon 2059) separately, and the prepared plasmid DNAs were added into the respective tubes in a concentration of 0.5–1.0 μg. These tubes were covered with aluminum foils respectively, and culturing was carried out at 30° C. overnight, and, then, the aluminum foils were removed, and culturing was continued at 30° C. under irradiation with light (1,000–2,000 luxes) for further six hours. 5–500 μl of these cell suspensions were taken out, and plated on a BG-11 agar medium (containing 1 μg/ml ampicillin, 1 mM sodium thiosulfate and 1.5% agar). These plates were subjected to culture under irradiation with light for 4 to 10 days.

(5) Comparison among the newly constructed shuttle vectors with regard to the transformation efficiency of A. nidulans R2 strain:

TABLE 1

Transformation of Anacystis nidulans R2 with new plasmids and pBAS18

| Plasmid | Deleted[a] sequences | Plasmid size (kb) | Transformation[b] efficiency (transformants/ μg DNA) | Relative[c] efficiency |
|---|---|---|---|---|
| pBAS18 | — | 12 | $8.1 \times 10^2$ | 1 |
| pBAS10 | 1.8-kb E-P | 10.1 | $1.8 \times 10^5$ | 187 |
| pBAS10R | 1.8-kb E-P | 10.1 | $2.5 \times 10^5$ | 260 |
| pBAX10 | 3.3-kb X-B | 8.7 | $5.2 \times 10^4$ | 46 |
| pBAX10R | 3.3-kb X-B | 8.7 | $5.1 \times 10^2$ | 0.4 |
| pBAX18 | 3.3-kb X-B and 1.8-kb E-P | 6.9 | $2.0 \times 10^5$ | 135 |
| pBAX18R | 3.3-kb X-B and 1.8-kb E-P | 6.9 | $2.0 \times 10^5$ | 142 |

[a]The deleted sequences, which are not essential segments for the replication of pBR322 in E. coli cells or pBA1 in A. nidulans R2 cells. 1.8-kb E-P; 1.8-kb Eco47III-PvuII segment of pBR322, 3.3-kb X-B; 3.3-kb XhoI-BamHI segment of pBA1.
[b]Each value for transformation frequency is an average of four determinations.
[c]Relative efficiency (RE) is expressed as follows:

$$RE = \frac{(\text{Transformation efficiency of the plasmid}) \times (\text{size of the plasmid (kb)})}{(\text{Transformation efficiency of pBAS18}) \times (\text{size of the pBAS18 (kb)})}$$

(6) Comparison among the constructed shuttle vectors with regard to the stability and the copy numbers in the host:

A. nidulans R2 strain cells transformed with each of the constructed vectors were cultured in 300 ml of BG-11 medium containing ampicillin (10 μg/ml) for 14 days. Each of the cultured cells were collected by means of centrifugation at 10000 rpm for eight minutes, and suspended respectively in 30 ml of SET solution (50 mM Tris-HCl, 50 mM EDTA, 20% sucrose, pH 7.6). 60 mg of lysozyme was added to the resulting suspension, and, then, incubation was conducted at 37° C. for two hours, and, next, proteinase K was added so that its concentration was incubated for a further 16 hours. A lytic mixture (1% SDS, 0.2N NaOH) was added to this reaction liquid, and, after the completion of bacteriolysis, plasmid DNA was extracted and formed by means of a normal SDS-alkali method. After the plasmid DNAs obtained from each transformant were treated with restriction enzyme EcoRI, each 0.2 μg of the plasmid DNA was placed on 1.0% of agarose gel, and was subjected to electrophoresis. After the electrophoresis was over, the gel was stained with ethidium bromide, and put on a transilluminator, and a photograph was taken (see FIG. 4).

Then, the plasmid DNA in the gel was transferred to a nitrocellulose membrane, and Southern hybridization was conducted with use of pBR322 as a probe, and, thus, the constructed shuttle vectors were compared with respect to the stability in the host and the copy number. After staining with ethidium, the agarose gel was dipped in a denaturing solution (1.5M NaCl, 0.5M NaOH), and was subjected to permeation for 30 minutes, and, thus, the plasmid DNA in the gel was denatured. Next, the gel was washed with sterilized water, transferred to a neutralizing solution (1.5M NaCl, 0.5M Tris-HCl, 1 mM EDTA, pH 7.2) and was shaken. After 15 minutes, the neutralizing solution was replaced with a new one, and the above process was repeated. After shaking for 15 minutes, the neutralizing solution was removed, and the gel was washed with sterilized water. Then, a blotting apparatus (Maniatis, et al., Molecular Cloning, Cold Spring Harbor Laboratory Press, 1982) was made by utilizing capillarity, and the plasmid DNA in the gel was transferred to a nitrocellulose membrane for one night by use of 20×SSC (1×SSC: 0.15M NaCl, 15 mM sodium citrate, pH 7.0). After the blotting was over, the nitrocellulose membrane was washed with 6×SSC, and was heat-dried at 80° C. for 10 minutes. Thereafter, DNA was put into a vacuum drier, which had been previously heated to 80° C., so as to be immobilized on a nitrocellulose membrane, and was treated for one hour.

This nitrocellulose membrane was dipped in 50 ml of a blocking solution [50% formamide, 10×Denhardt's solution (1×Denhardt's solution: 0.02% bovine serum albumin, 0.02% polyvinyl pyrrolidone, 0.02% Ficoll), 4×SET (1×SET: 0.15M NaCl, 30 mM Tris-HCl, 1 mM EDTA, pH 8.0), 0.1% SDS], and was incubated at 37° C. for two hours. Then, the membrane was put in a polyethylene bag, into which was fed 20 ml of prehybridization solution [50% formamide, 2×Denhardt×s solution, 4×SET, 6% polyethylene glycol 6000, 0.1% SDS, 50 μg/ml denatured salmon sperm DNA]. The thus treated membrane was incubated at 37° C. After two hours, pBR322 DNA labelled with peroxidase with use of Labezyme-POD (made by Wako Junyaku Kogyo) was added to the prehybridization solution, and hybridization was carried out by conducting incubation at 37° C. for a further 12 hours. After the hybridization was over, the membrane was taken out and washed lightly with a cleaning fluid [50% formamide, 0.4% SDS, 0.5×SSC]. Then, the membrane was dipped in 50 ml of cleaning fluid and was shaken at 37° C. for 20 minutes. The cleaning fluid was replaced with a new one, and the membrane was shaken at 37° C. for 20 minutes in the same manner (20 minutes×3). Thereafter, the cleaning fluid was removed, and the membrane was washed with 2×SSC two to three times each for two minutes, and, then, was cleansed by being shaken in 2×SSC three times each for 20 minutes. The cleansed membrane was placed on a filter paper to remove moisture, and was dipped in 20 ml of an enzyme reaction staining liquid [20×enzyme reaction buffer (1 ml), a solution of chloronaphthol dissolved in ethanol (1 ml), 30% aqueous solution of hydrogen peroxide (20 μl)]. A reaction occurred while shaking the above liquid until a preferable stained image was obtained.

The plasmid DNA transferred to the nitrocellulose membrane by the above operation was tinged with pale purple. Resultantly, in shuttle vectors pBAS18, pBAX10 and pBAX10R which had a rop region in their sequence, plural numbers of bands different from those of the vector DNA used for the transformation of the host were observed (see FIG. 4). In shuttle vectors pBAS10, pBAS10R, pBAX18 and pBAX18R which had no rop region, on the other hand, only such bands as showed the same mobility as the vector DNA used for the transformation of the host were observed (see FIG. 4). These facts seem to mean that, when a rop region is contained in the sequence of a shuttle vector, the vector is unstable since it is liable to cause recombination with an endogenous plasmid DNA in a host.

Figure 4:
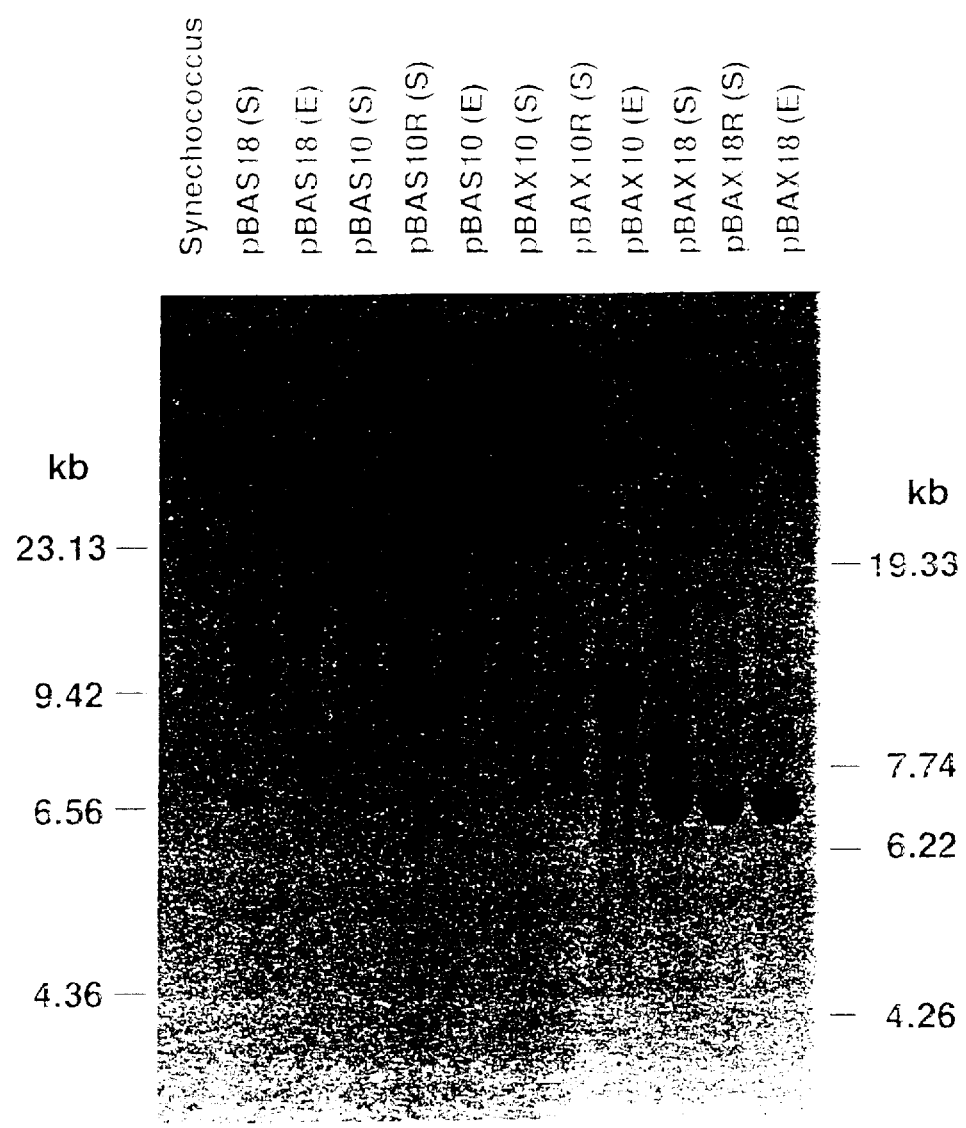
FIG. 4 is a photograph of a stained nitrocellulose membrane prepared in accordance with Example 4.

Besides, it is found that, among the newly constructed shuttle vectors, there is a clear difference in the copy numbers in a host (see FIG. 4). Thus, by measuring the light and shade and area of this color with use of a densitometer, the copy numbers of respective shuttle vectors in a host were compared with one another. As a result, when the copy number of pBAS18 in a host was taken as 1 (one), then pBAS18 : pBAS10 : pBAS10R : pBAX10 : pBAX10R : pBAX18 : pBAX18R=1 : 3.27 : 5.06 : 0.43 : 0.54 : 3.63 : 4.60 (these values are the average of the values obtained from three experiments). The copy numbers in a host of shuttle vectors pBAS18, pBAX10 and PBAX10R which had a rop region in their sequence were smaller than those of shuttle vectors pBAS10, pBAS10R, pBAX18 and pBAX18R which had no rop region. It is presumed that shuttle vectors pBAS18, pBAX10 and pBAX10R which have a rop region in their sequence have a structural influence (of making replication hard to occur) on account of the presence of the rop region on the occasion of the replication of plasmid in a host; accordingly, the copy numbers are kept on a low level. On the other hand, it is considered that shuttle vectors PBAS10, pBAS10R, pBAX18 and pBAX18R which have no rop region, free from the structural influence of rop region, can maintain large and stable copy numbers in a host.

INDUSTRIAL APPLICABILITY

The plasmid of this invention can be prepared in a large amount using *Escherichia coli* and replication in the cells of both *Escherichia coli* and cyanobacteria, and are useful as a shuttle vector for expression of various structural genes in the cells of cyanobacteria.

We claim:

1. A plasmid pBAX18 having a size of about 6.9 kb which replicates in *Escherichia coli* and cyanobacteria, and is characterized by the restriction endonuclease map shown in FIG. 1.

2. A plasmid pBAX20 having a size of about 5.8 kb which replicates in *Escherichia coli* and cyanobacteria, and is characterized by the restriction endonuclease map shown in FIG. 2.

* * * * *